(12) United States Patent
Hadizadeh Hafshejani et al.

(10) Patent No.: US 10,270,461 B1
(45) Date of Patent: Apr. 23, 2019

(54) NON-UNIFORM SAMPLING IMPLEMENTATION

(71) Applicants: Ehsan Hadizadeh Hafshejani, Vancouver (CA); Ali Fotowat-Ahmady, Great Falls, VA (US); Kiomars Anvari, Walnut Creek, CA (US)

(72) Inventors: Ehsan Hadizadeh Hafshejani, Vancouver (CA); Ali Fotowat-Ahmady, Great Falls, VA (US); Kiomars Anvari, Walnut Creek, CA (US)

(73) Assignee: Kiomars Anvari, Walnut Creek, CA (US)

( * ) Notice: Subject to any disclaimer, the term of this patent is extended or adjusted under 35 U.S.C. 154(b) by 0 days.

(21) Appl. No.: 16/116,868

(22) Filed: Aug. 29, 2018

Related U.S. Application Data

(63) Continuation of application No. 16/114,346, filed on Aug. 28, 2018.

(51) Int. Cl.
| | |
|---|---|
| H03M 1/00 | (2006.01) |
| H03M 1/12 | (2006.01) |
| H03K 21/38 | (2006.01) |
| H03K 5/24 | (2006.01) |
| G11C 27/02 | (2006.01) |
| H03M 1/56 | (2006.01) |
| H03M 1/54 | (2006.01) |
| H03M 1/52 | (2006.01) |

(52) U.S. Cl.
CPC .......... *H03M 1/1265* (2013.01); *G11C 27/02* (2013.01); *H03K 5/24* (2013.01); *H03K 21/38* (2013.01); *H03M 1/124* (2013.01); *H03M 1/126* (2013.01); *H03M 1/1245* (2013.01); *H03M 1/52* (2013.01); *H03M 1/54* (2013.01); *H03M 1/56* (2013.01)

(58) Field of Classification Search
CPC .... H03M 1/1245; H03M 1/126; H03M 1/124; H03M 1/52; H03M 1/54; H03M 1/56; H03M 1/12
USPC ................ 341/123, 122, 124, 120, 155, 127
See application file for complete search history.

(56) References Cited

U.S. PATENT DOCUMENTS

2012/0293350 A1* 11/2012 Redfern .................. H03M 1/18
341/122

\* cited by examiner

*Primary Examiner* — Joseph J Lauture

(57) ABSTRACT

This application discloses an implementation of a novel non-uniform sampling technique for a burst type signal. A simple circuit is developed that implements an analog computation of a complex digital calculation to skip the unnecessary samples and choose the optimum next sample. Then the optimum samples are selected for further processing which results in overall cost and power consumption reduction.

5 Claims, 17 Drawing Sheets

Figure 3
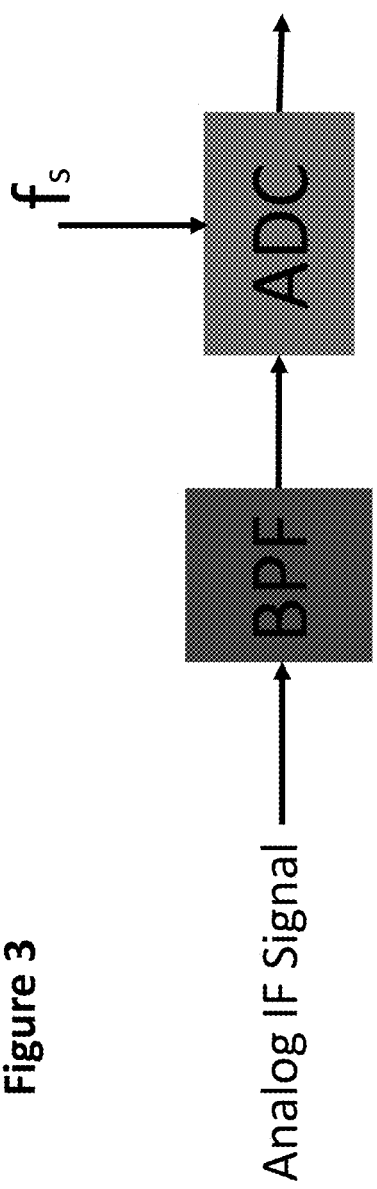
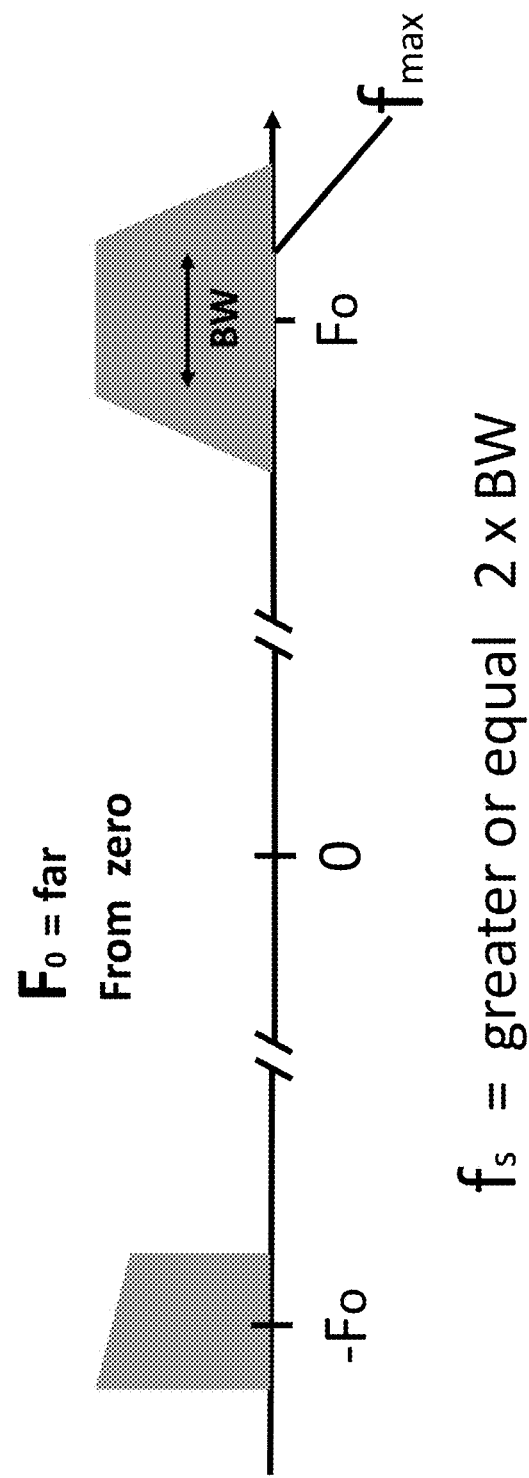

Figure 4 Sub-Harmonic IF Sampling

NON-UNIFORM SAMPLING IMPLEMENTATION

The application claims priority to the following related application and included here is as a reference.

Nonprovisional application: U.S. patent application Ser. No. 16/114,346 filed Aug. 28, 2018, and entitled "A NOVEL NON-UNIFORM SAMPLING".

BACKGROUND

In the field of digital signal processing, the sampling theorem is a fundamental bridge between continuous-time signals (often called "analog signals") and discrete-time signals (often called "digital signals"). It establishes a sufficient condition for a sample rate that permits a discrete sequence of samples to capture all the information from a continuous-time signal of finite bandwidth.

The continuous analog data must be sampled at discrete intervals that must be carefully chosen to ensure an accurate representation of the original analog signal. It is clear that the more samples taken (faster sampling rate), the more accurate the digital representation, but if fewer samples are taken (lower sampling rates), a point is reached where critical information about the signal is actually lost.

The Nyquist Theorem, also known as the sampling theorem, is a principle that engineers follow in the digitization of analog signals. For analog-to-digital conversion to result in a faithful reproduction of the signal; according to the Nyquist Theorem, the sampling rate must be at least twice the highest analog frequency component as shown in FIG. 1.

There are times that the analog signal spectrum is slightly shifted from the zero Hz frequency as shown in FIG. 2. This type of signal is called low intermediate frequency (IF) signal. In this case there are two approaches. One is to shift the analog signal spectrum to zero Hz in analog domain and then similar to FIG. 1 use Nyquist sampling and digitize the analog signal. In the first approach there is need for analog circuitry for shifting the spectrum to zero Hz which results in cost and power consumption. In a second approach Nyquist theorem is used to digitized the low IF analog signal and then shift the spectrum in digital domain to zero Hz. This approach requires higher sampling rate, a higher rate analog-to-digital convertor and slightly signal processing in digital domain.

In another scenario the analog signal is centered at a high IF frequency as shown in FIG. 3. In this scenario there are three solutions. One similar to low IF down convert the analog signal to zero Hz frequency and then digitized. Again this approach results in cost and power consumption. The second approach is to sample the high IF analog signal which requires very high rate analog-to-digital convertor and considerable signal processing that results in cost and power consumption. The third approach is to use sub-harmonic sampling. In sub-harmonic sampling in order to be able to recover analog signal information in digital domain the sampling rate should be equal or higher than twice the bandwidth of the analog signal. The choice of the sampling rate needs to simplify the required signal processing in digital domain. FIG. 4 demonstrate how sub-harmonic sampling is used to digitize and subsequently shift the digital signal to zero Hz for a complex signal with real and imaginary components.

If the sampling rate is smaller than what was defined above, then a phenomenon called aliasing will occur in the analog signal bandwidth as shown in FIG. 5. It can be seen that aliasing affects the dynamic range of the signal since the upper part of the signal spectrum is affected. This condition will result in reduction in overall signal-to-noise at the higher frequencies, and could result in the distortion due to aliased out-of-band tones or harmonics as shown in FIG. 5.

It should be cleared by now, that for a given analog input bandwidth; the requirements for anti-aliasing filter are related not only to the sampling rate, fs, but also to the desired system dynamic range. For burst type analog signals that have harmonics spread over a very large bandwidth like the one shown in FIG. 6 defining the requirements of the anti-aliasing filter is even more difficult. One also has to consider the limitations of analog-to-digital quantization noise and other non-linearity.

This application discloses an implementation of a novel non-uniform sampling technique for a burst type signal. A simple circuit is developed that implements an analog computation of a complex digital calculation to skip the unnecessary samples and choose the optimum next sample. Then the optimum samples are selected for further processing which results in overall cost and power consumption reduction.

BRIEF DESCRIPTION OF THE DRAWINGS

FIG. 3 shows sub-harmonic IF sampling
FIG. 4 illustrate detail of sampling frequency for sub-harmonic IF sampling

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
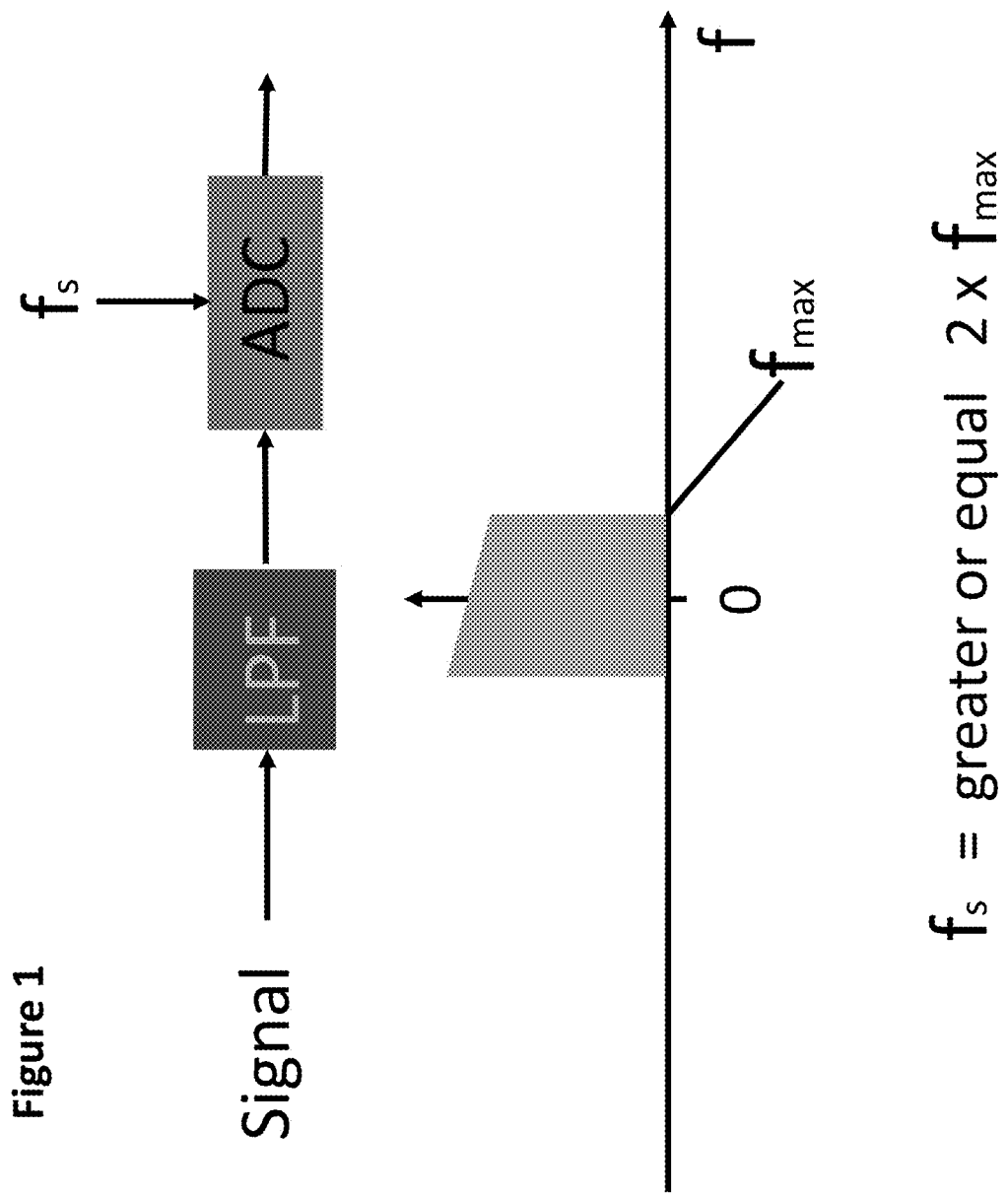
FIG. 1 illustrate Nyquist sampling
Figure 2:
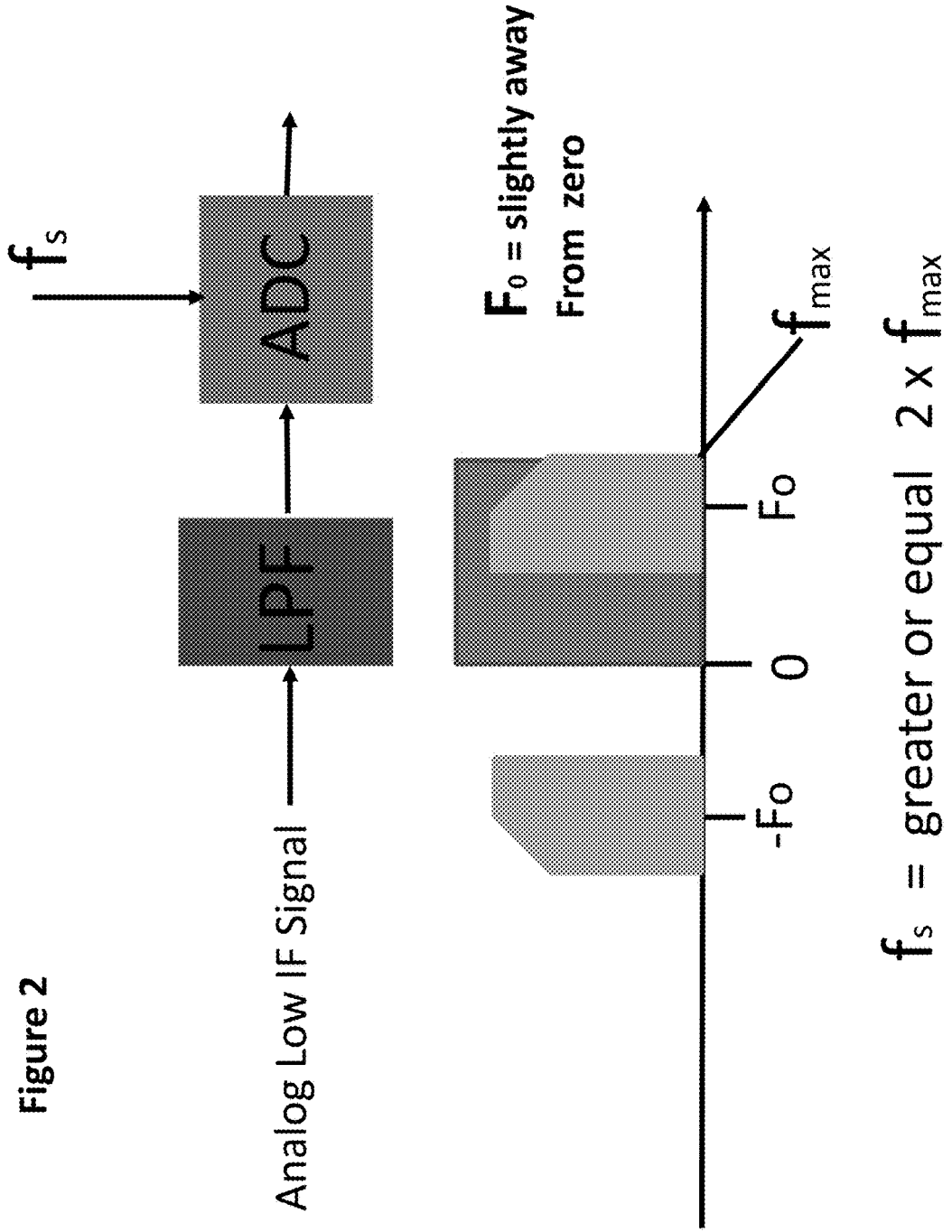
FIG. 2 shows low IF sampling
Figure 4:
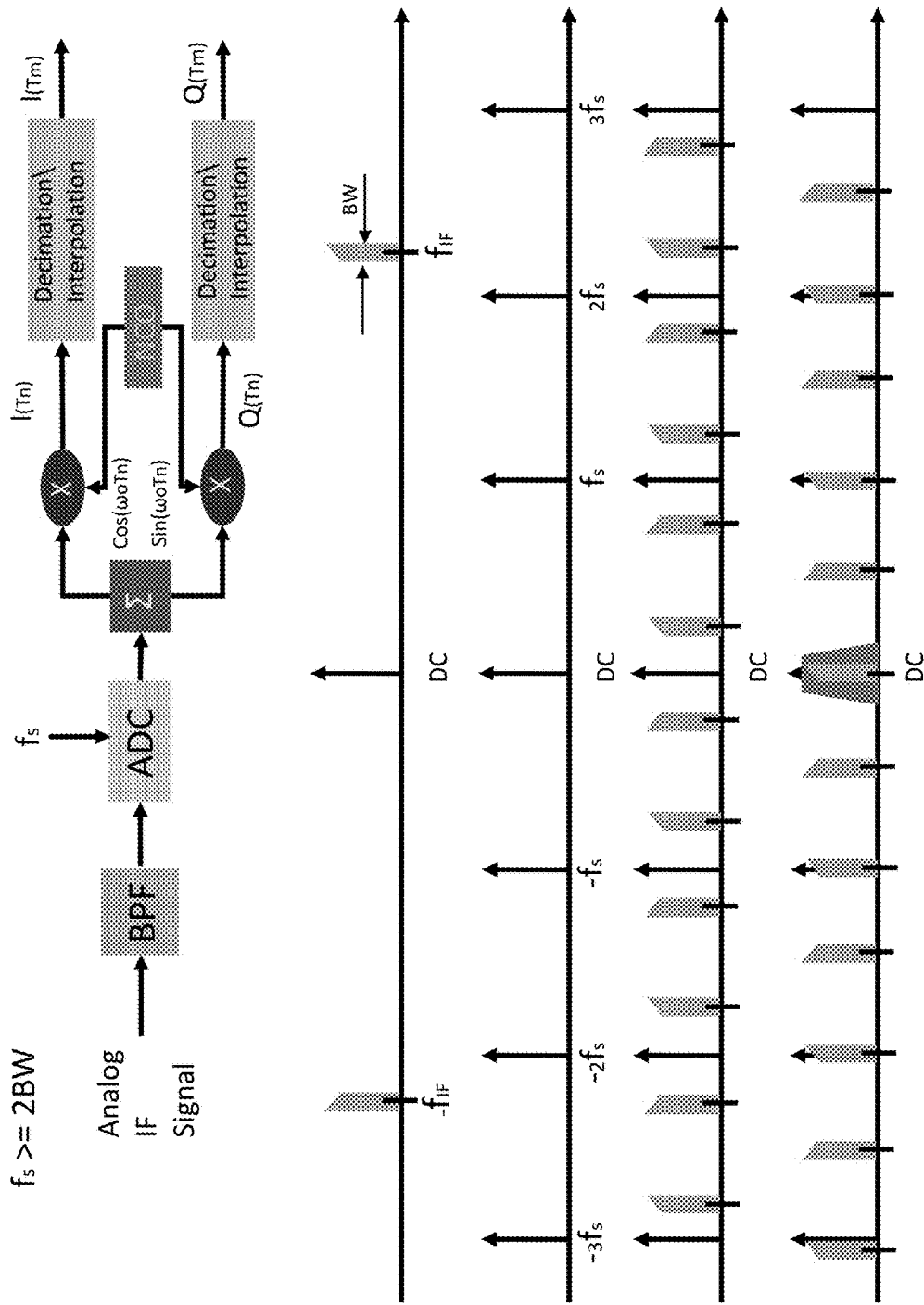
Figure 5:
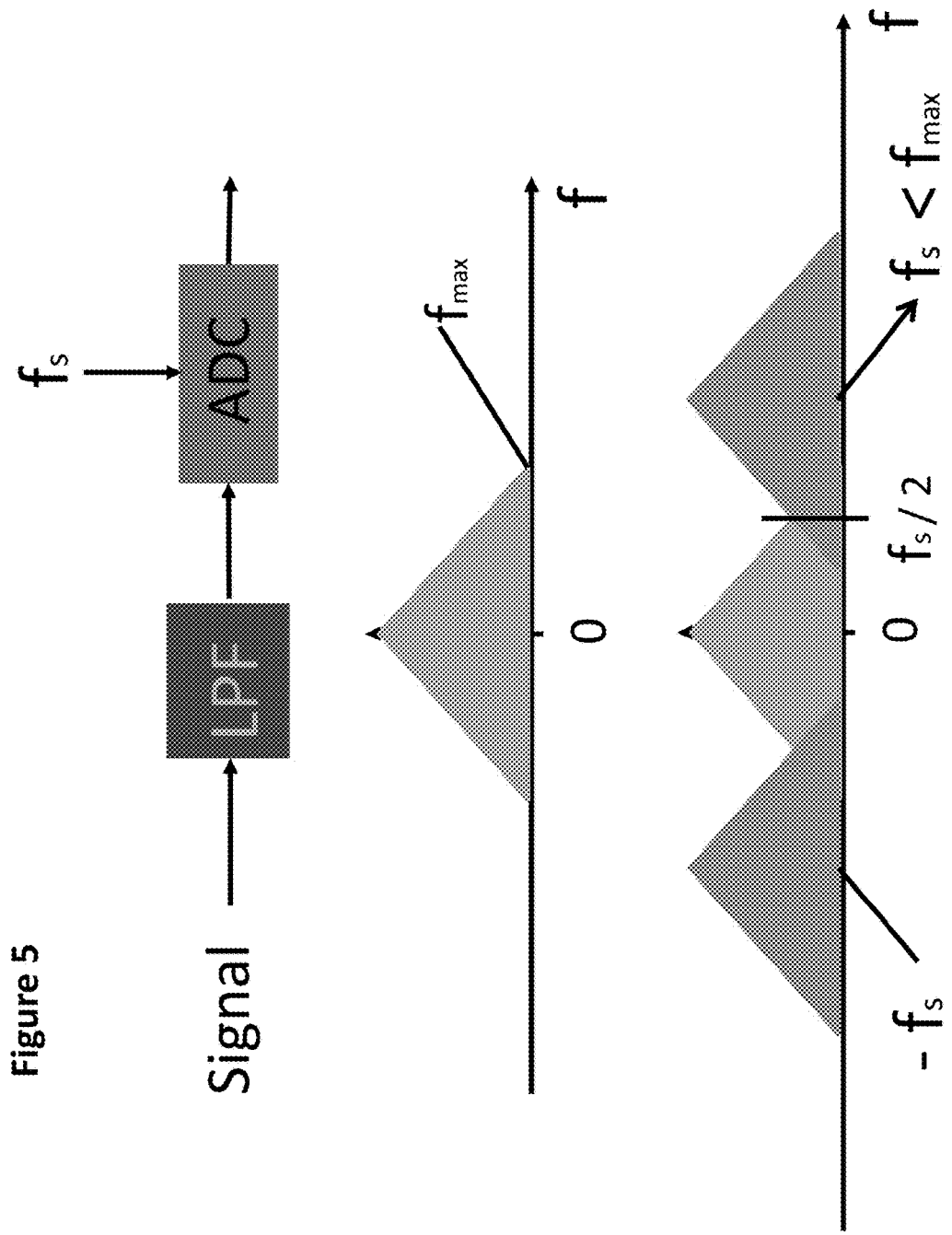
FIG. 5 shows the effect of aliasing due to under sampling
Figure 6:
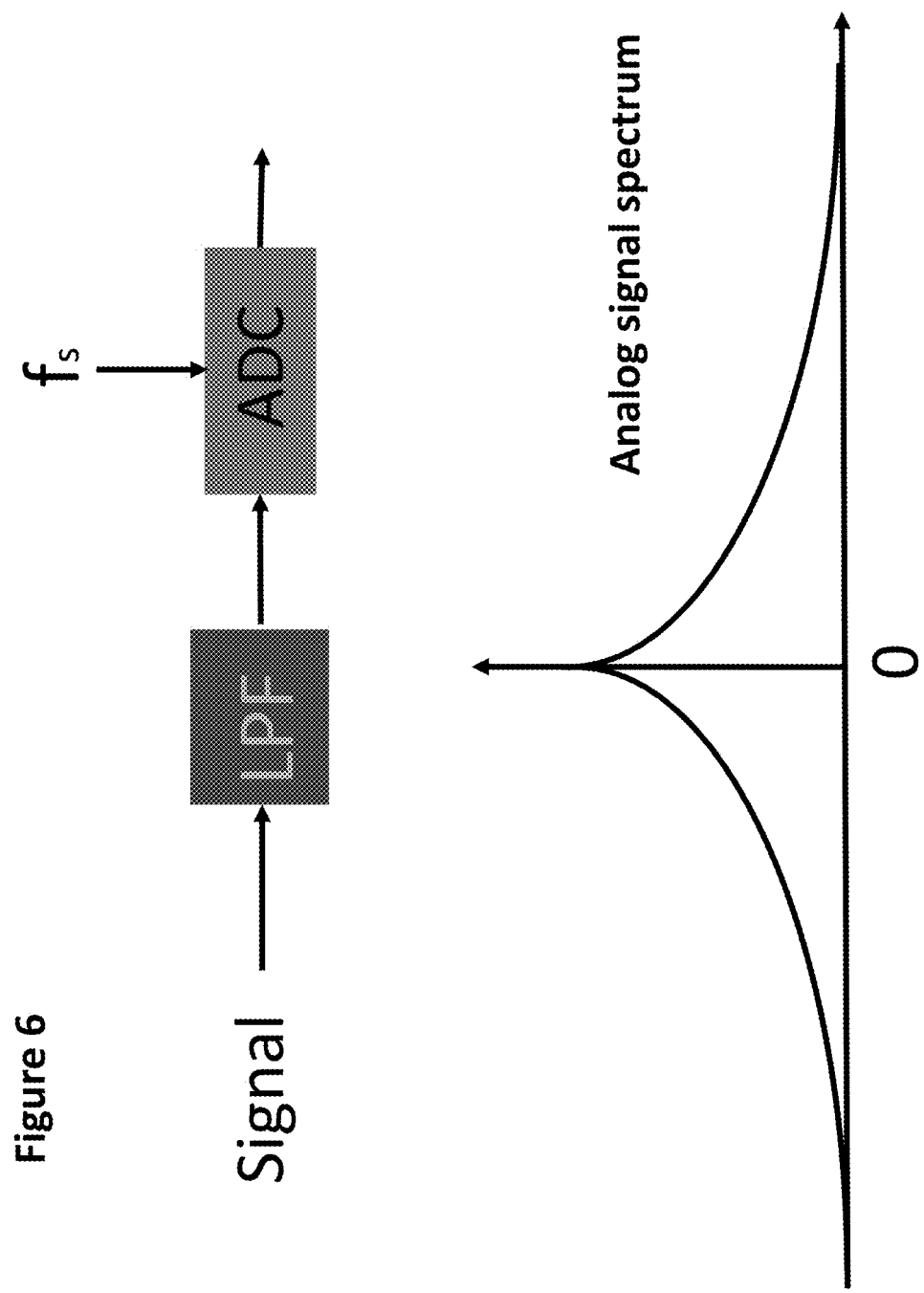
FIG. 6 shows the spectrum of a burst type analog signal
Figure 7:
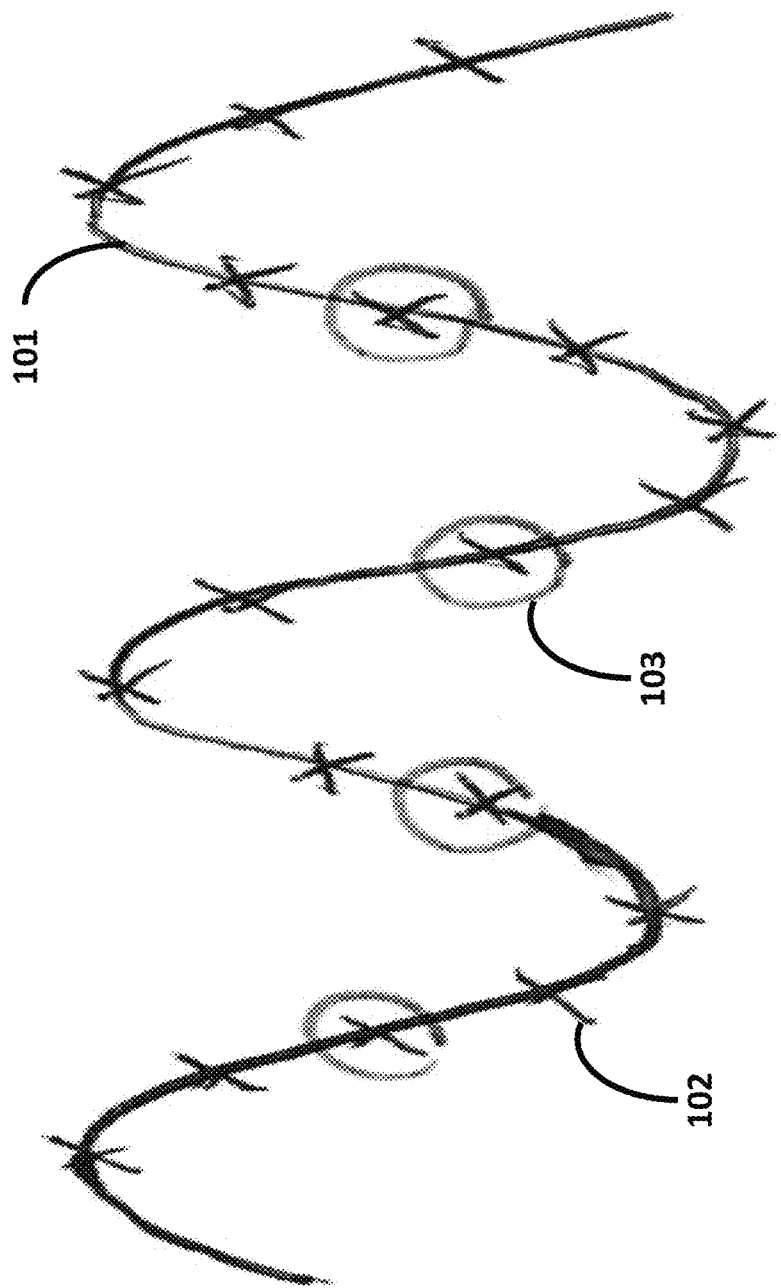
FIG. 7 illustrates a sampled sinusoidal signal

FIG. 7 depicts an over sampled signal 100. A sinusoidal signal 101 is over sampled and represented by samples 102. According to Nyquist theorem for sinusoidal signal 101 only two samples per period is requires. Therefore circled samples 103 for sinusoidal signal 101 are redundant.

In one embodiment of over sampled signal 100, the redundant samples 103 can be identified and removed without loss of signal fidelity.

Figure 8:
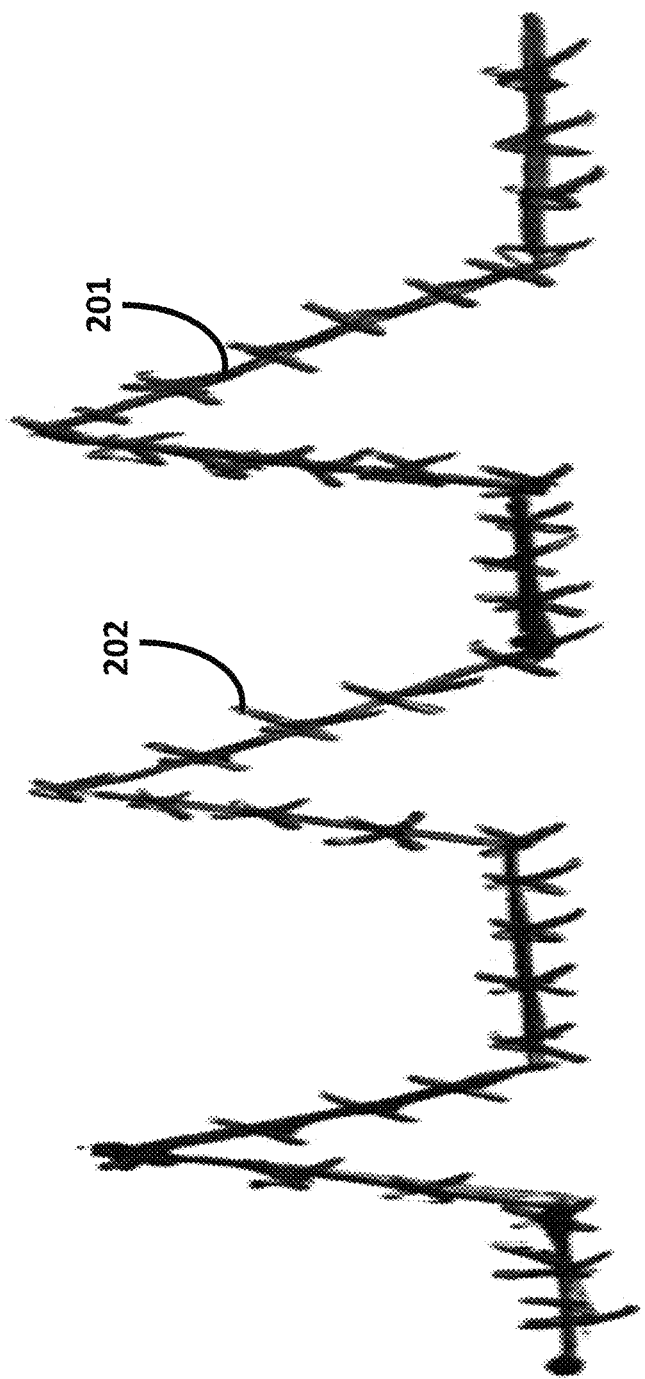
FIG. 8 depicts an over sampled bust type signal

FIG. 8 illustrate a sampled burst signal 200. The burst signal comprises of periodic bursts 201. The burst signal 200 is sampled based on Nyquist theorem and represented by samples 202. It is clear from periodic burst signal 201 that there are considerable redundant samples 202 during one period of the burst both in the flat part of the period and during the burst.

Figure 9:
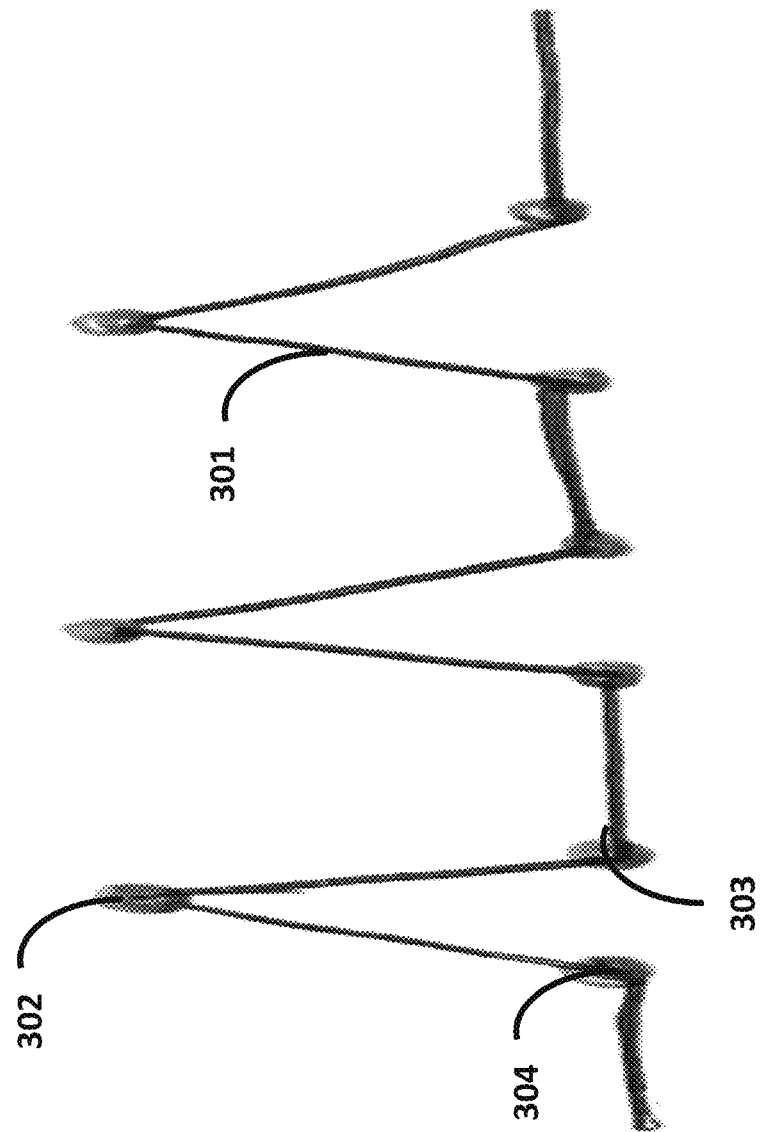
FIG. 9 shows the required samples for a burst type signal
FIG. 10 illustrate derivative of consecutive samples

FIG. 9 illustrate a sampled burst signal 300. The burst 301 does not require multiple samples for most of its period except during the time it burst. There are three sample points 302, 303, and 304 in burst 301 that carry the required information for continued processing.

In one embodiment of burst signal 300, sample 304 at the start of burst 301, sample 302 at the peak of the burst 301, and sample 303 at the end of the burst 301 are sufficient for further processing of a burst signal.

Figure 10:
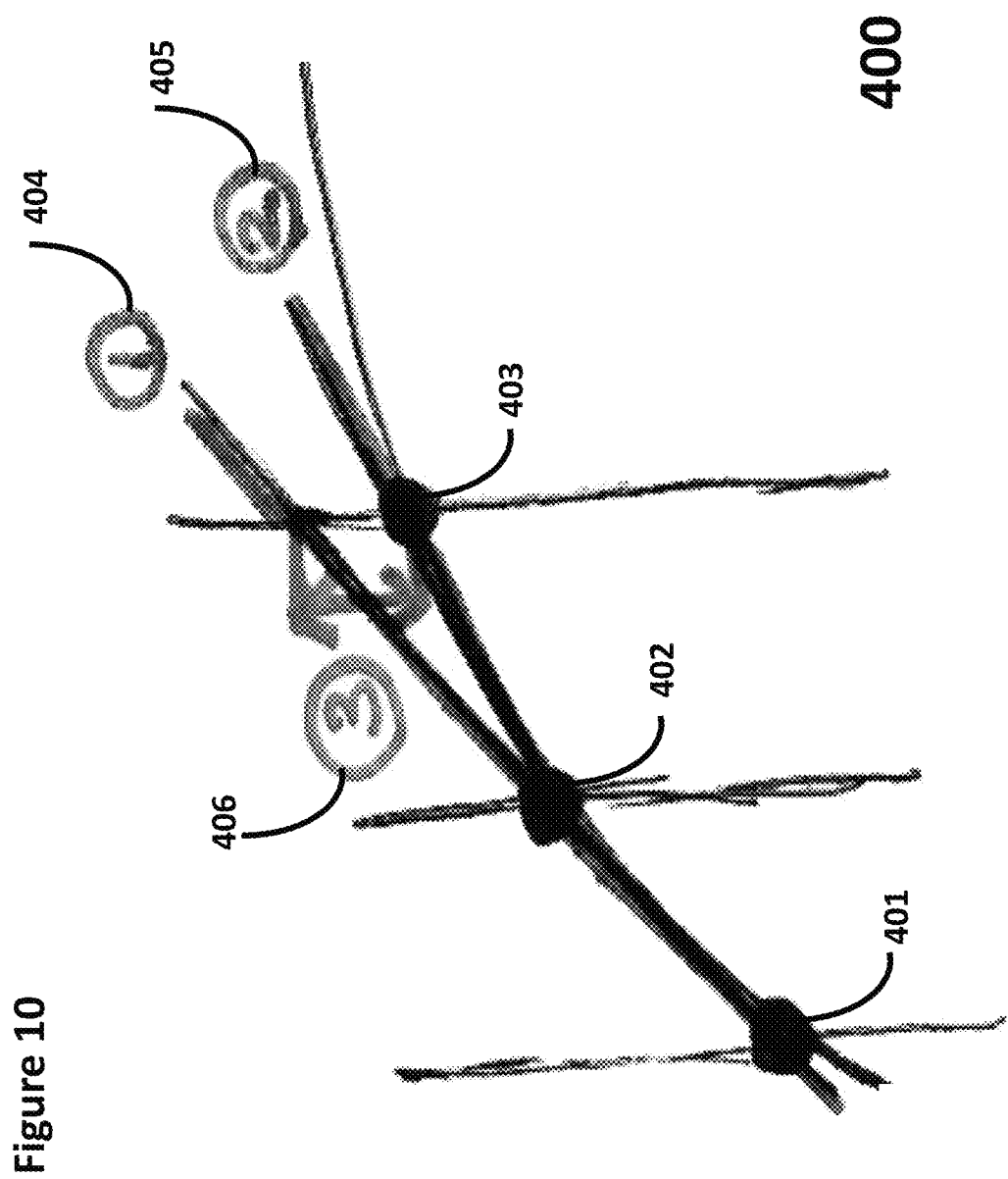

FIG. 10 depicts consecutive sample pairs derivative 400. Derivative of two samples 401 and 402 results in slop 404 and derivative of two samples 402 and 403 results in slop 405. If the difference between these two derivative 406 is zero or negligible then sample 402 can be eliminated.

In one embodiment of consecutive sample pair derivative 400, consecutive sample pair derivatives is used to determine which sample of an analog signal can be eliminated without loss of signal fidelity.

Figure 11:
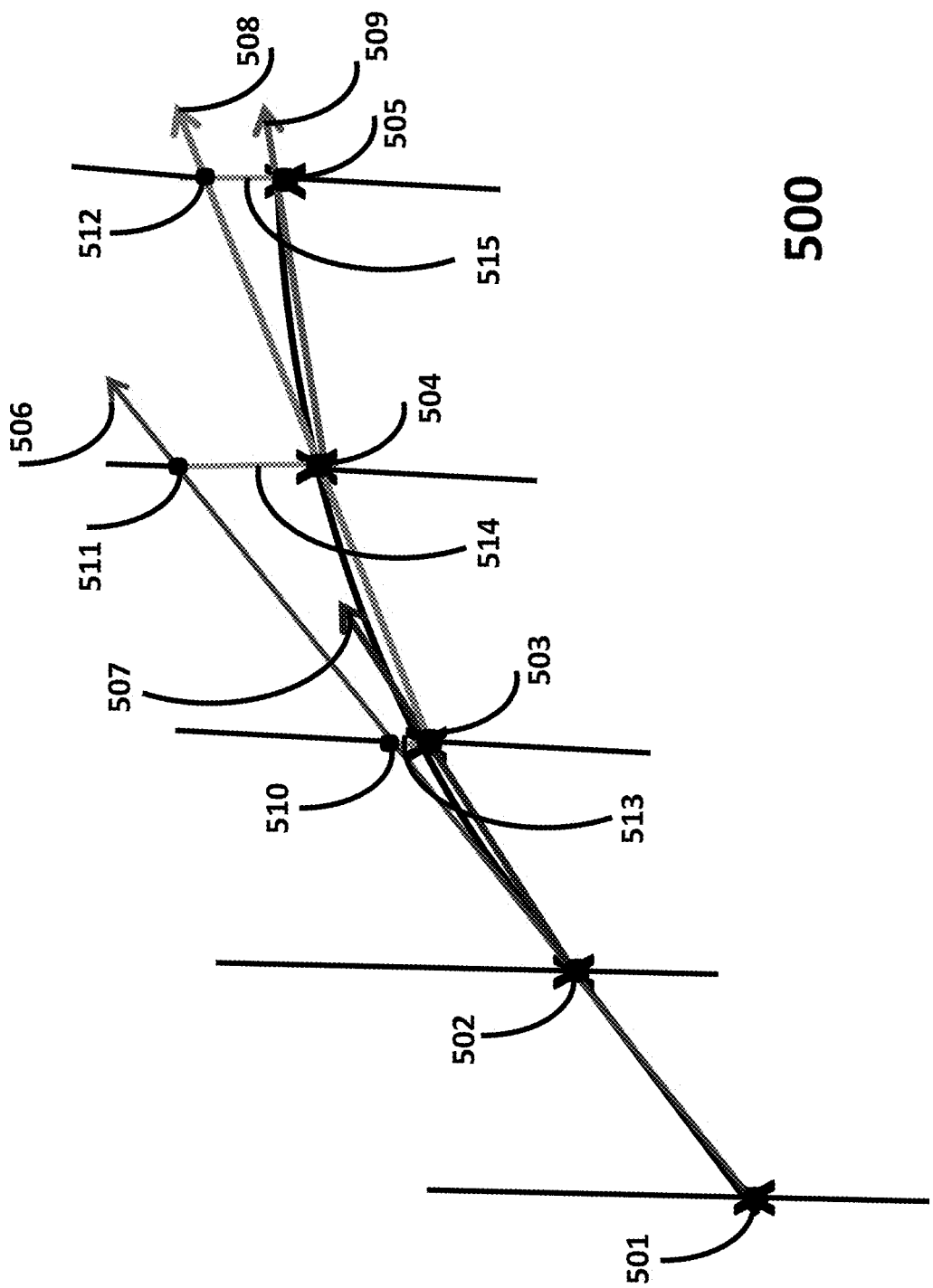
FIG. 11 depicts how to reduce the number of uniform samples

FIG. 11 illustrate a non-uniform sampling technique 500. In general non-uniform sampling 500 facilitates elimination of samples in an over sampled analog signal using derivatives of consecutive sample pairs. The samples 501, 502, 503, 504, and 505 of an over sampled analog signal are used to find slops 506, 507, 508, and 509, determine estimated values 510, 511 and 512 for samples 503, 504 and 505, and calculate differences 513, 514, and 515 between estimated values 510, 511 and 512 and the real values 503, 504, and 505 respectively. Derivative of sample pair 501 and 502 results in slop 506, derivative of sample pair 502 and 503 results in slop 507, derivative of sample pair 503 and 504 produces slop 508, and derivative of sample pair 504 and 505 results in slop 509. Slop 506 is used to find estimated value 510 for sample 503. If 513 the difference between real value of sample 503 and the estimated value 510 is smaller than a specified threshold, it allows sample 502 to be eliminated. Since sample 502 is eliminated slop 506 represents the derivative of sample pair 501 and 503 and is used to find an estimated value 511 for sample 504. The difference 514 between real value of sample 504 and its estimated value is higher than a specified threshold and therefore, sample 503 is not eliminated. Slop 508 representing derivative of sample pair 503 and 504 is used to find an estimated value 512 for sample 505. Since the difference 515 between real value of sample 505 and its estimated value 512 is higher than a specified threshold sample 505 is kept and the process continues for following samples.

In one embodiment of non-uniform sampling technique 500, a derivative of a pair of consecutive samples is used to calculate the slop of the line connecting the two samples In one embodiment of non-uniform sampling technique 500, the slop of the line connecting a pair of consecutive samples is used to find an estimated value for the sample followed the pair of consecutive samples.

In another embodiment of non-uniform sampling technique 500, the difference between the estimated value and real value of the sample followed the pair of consecutive samples is used to decide whether the second sample in the pair of consecutive samples can be eliminated.

In one embodiment of non-uniform sampling technique 500, a threshold for the difference of the estimated and the real value of the sample followed the pair of consecutive samples is used to decide if the second sample in the pair of consecutive samples can be eliminated.

Figure 12:
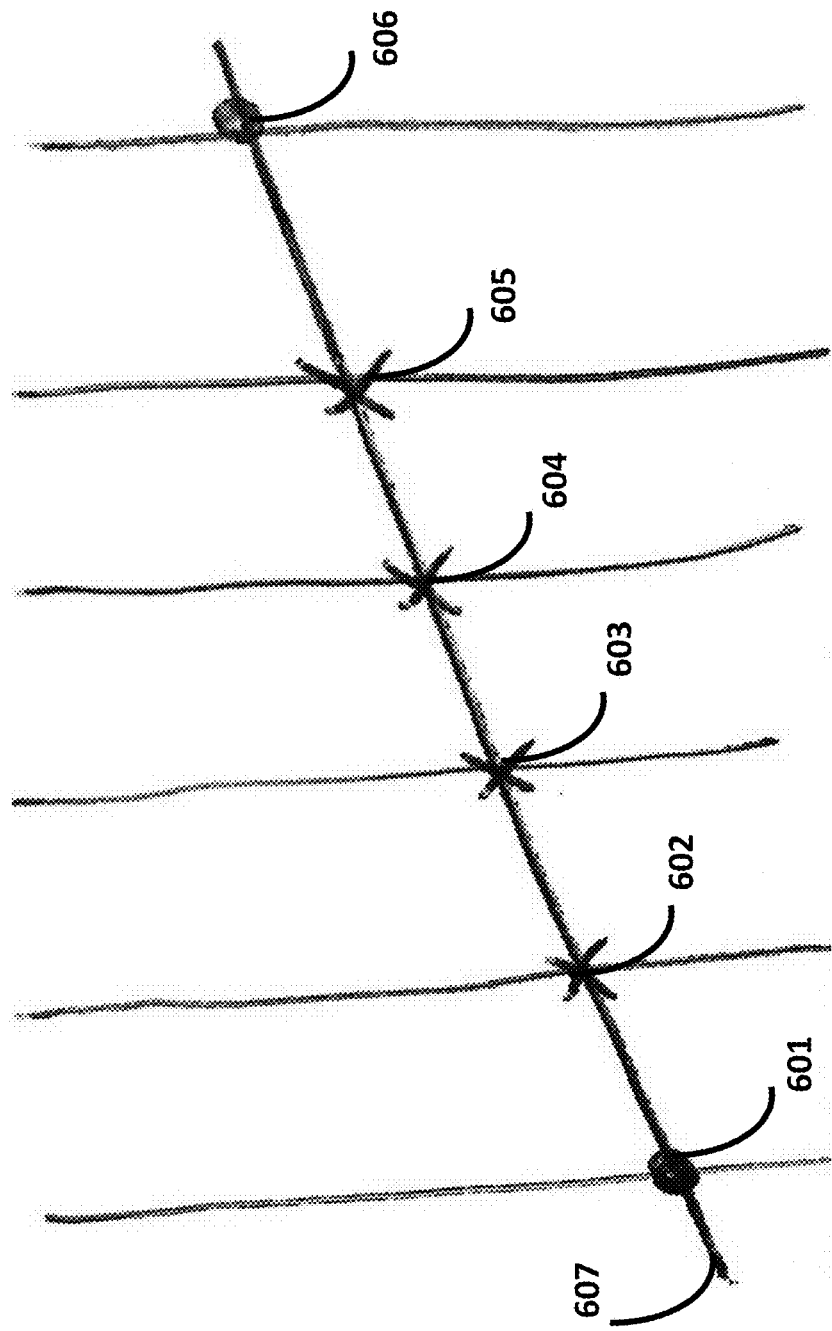
FIG. 12 shows the case when the slop of consecutive samples has minimum change
FIG. 13 illustrate scenario I of a sampled analog signal
FIG. 14 illustrate scenario II of a sampled analog signal

FIG. 12 shows sample elimination criteria 600. In general sample elimination criteria is based on a threshold which depends on type of analog signal and the amount of over sampling. Samples 601, 602, 603, 604, 605, and 606 represent a time window of an over sampled analog signal. The difference between derivative of consecutive sample pair 601, and 602 and the consecutive sample pair 602, and 603 is below a predefined threshold and results in elimination of sample 602. The difference between derivative of consecutive sample pair 601, and 603 and the consecutive sample pair 603, and 604 is also below a predefined threshold and results in elimination of sample 603. If this process is continued samples 602, 603, 604 and 605 are eliminated. However, the number of samples in a row that can be eliminated depends on the fidelity and integrity of over sampled analog signal and need to be limited to an acceptable number.

In one embodiment of sample elimination criteria 600, the number of samples in a row that can be eliminated needs to be limited to a figure that the fidelity and integrity of over sampled analog signal is maintained.

Figure 13:
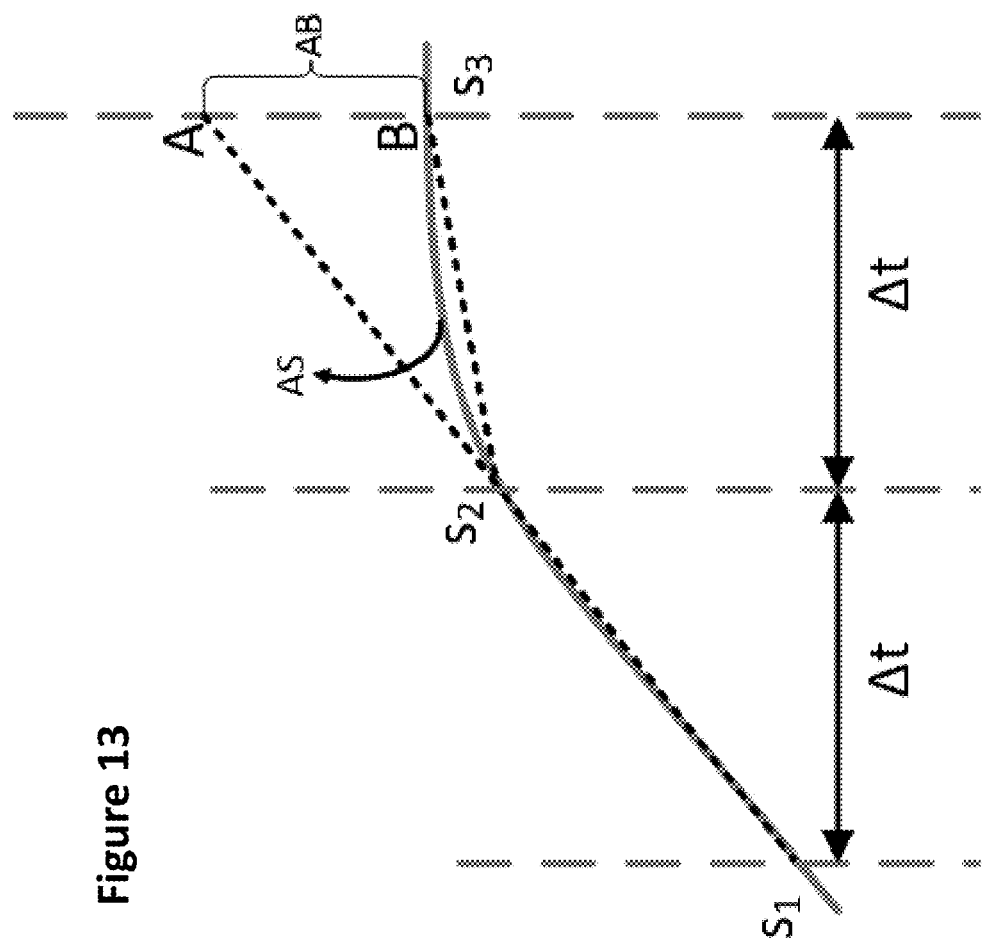

FIG. 13 shows scenario I of an analog signal (AS) with 3 samples S1, S2, and S3. "AB" which is proportional to slope change of the line connecting S1 and S2 and the line connecting S2 and S3 is represented by equation 1 (Eq. 1)

$$|(S_2-S_1/\Delta t - S_3-S_2/\Delta t)|\Delta t \qquad \text{(Eq. 1)}$$

Where $\Delta t$ is sampling time interval. In this scenario "AB" is large and no sample can be eliminated.

Figure 14:
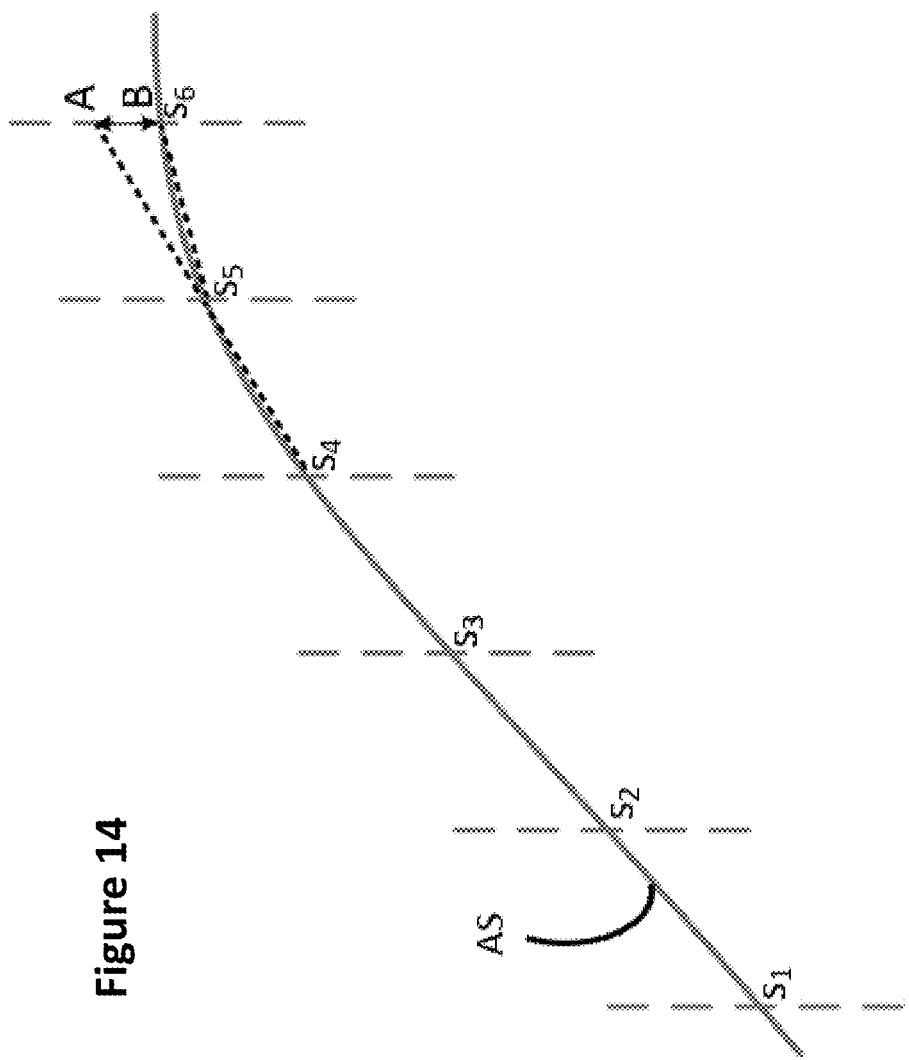

FIG. 14 shows scenario II of an analog signal (AS) with 6 samples S1, S2, S3, S4, S5 and S6. "AB" which is proportional to slope change of the line connecting S1, S2, S3, S4, S5, and the line connecting S5 and S6 is represented by equation 2 (Eq. 2)

$$|(S_5-S_1/4\Delta t - S_6-S_5/\Delta t)|\Delta t \qquad \text{(Eq. 2)}$$

Where $\Delta t$ is sampling time interval. And from this calculation it is decided that samples $S_2$, $S_3$ and $S_4$ can be eliminated.

Using a strictly digital methodology all samples $S_1$ thorough $S_6$ must be digitized and equations similar to Eq. 1 and Eq. 2 iteratively computed and compared against a threshold parameter which decides if a sample is to be eliminated. A means of digital counting of the samples is needed which in the case of FIG. 14 will indicate that 4 consecutive samples can be eliminated.

This digital computation-based analysis requires multi sample/hold circuits, ND converters and possibly a floating point processor for addition, subtraction, multiplication and division.

Figure 15:
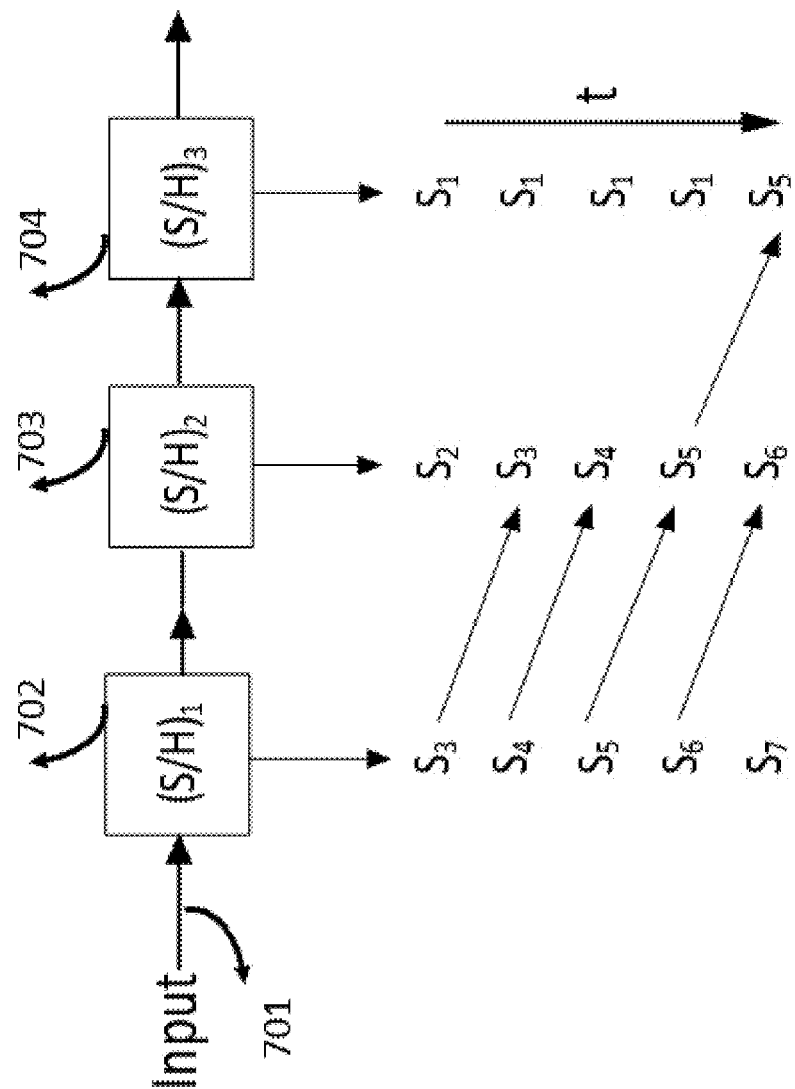
FIG. 15 shows an implementation of 3 sample/hold scheme

FIG. 15 depicts block diagram of a simple analog sampling 700. The analog sampling 700 implementation uses 3 sample/hold (S/H) blocks 702, 703, and 704 for analog signal shown in FIG. 14. The chain of multiple S/H circuits eliminates the need for multiple ND converters.

In one embodiment sample and hold S/H 702 continuously samples the input analog signal 701 and produces samples S1 to S7. Sample S1 is transferred to S/H 703 and then S/H 704. Sample S2 to S6 are transferred to S/H 703

In another embodiment the data from S/H 703 is only transmitted to S/H 704 when the length of |AB|>ϵ as shown in FIG. 14.

Figure 16:
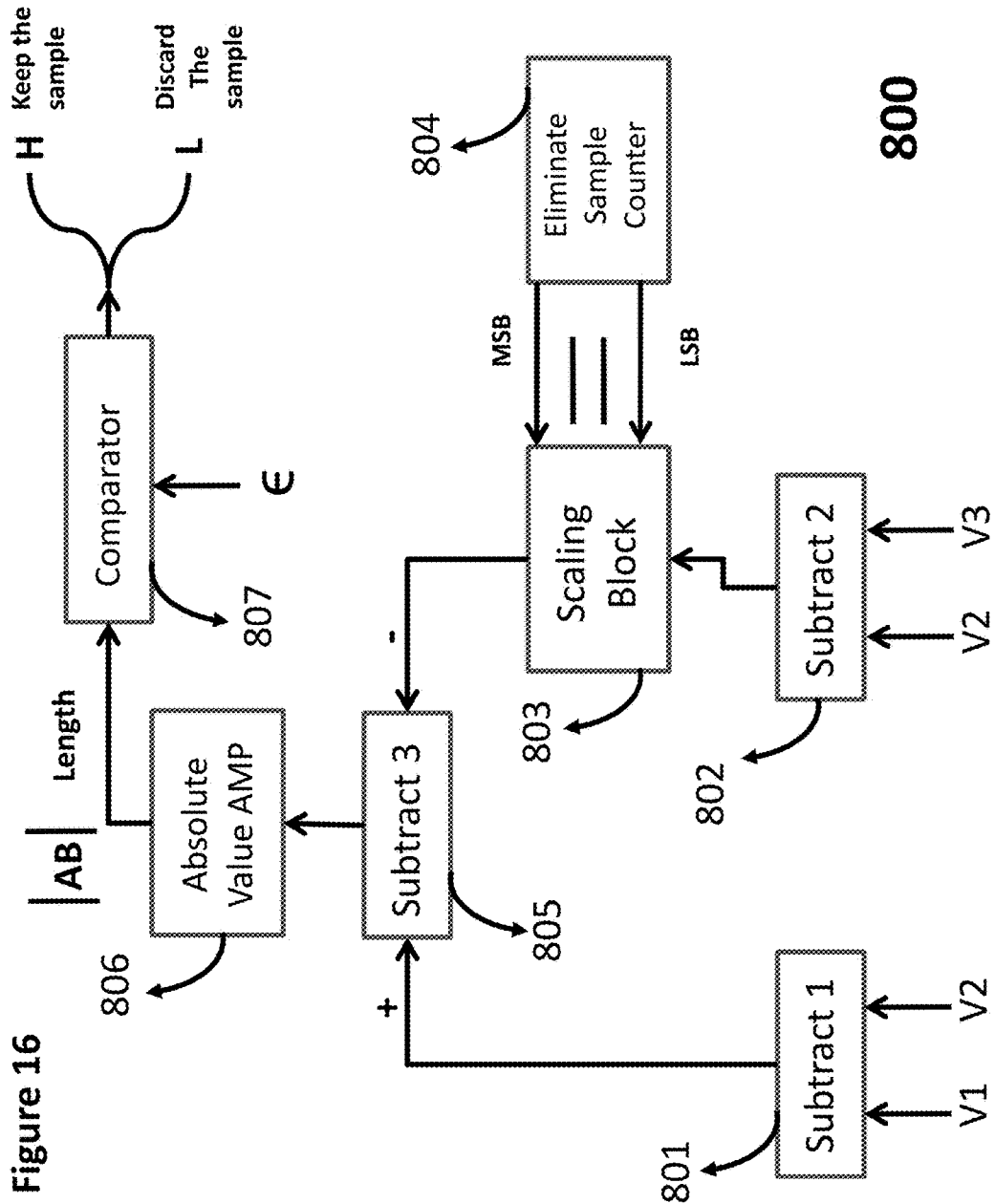
FIG. 16 depicts block diagram of the decision circuit

FIG. 16 shows a general block diagram of the decision circuit 800. Decision circuit 800 is aimed for FIG. 14, samples S1, S2, S3, S4, S5, S6, etc and Eq. 2. The voltages V1, V2, and V3 represents the value of one of the samples S1, S2, S3, S4, S5, S6 etc.

Decision circuit 800 among other things includes, subtract blocks 801, 802, and 805, scaling block 803, eliminated sample counter 804, absolute value amplifier 806, and comparator 807.

In one embodiment of decision circuit 800, voltages V2 and V3 used by subtract 802 can come from non-consecutive samples due to number of eliminated samples between them.

In one embodiment of decision circuit 800, voltages V1 and V2 used by subtract 801 can be from consecutive samples.

In another embodiment of decision circuit 800 the output of subtract block 803 is divided (scaled) back based on the number of eliminated samples stored in eliminated sample counter 804. This is done in the scaling block 803 which receives the number of eliminated samples from the eliminated sample counter 804.

In one embodiment of decision circuit 800, the outputs of the subtract block 801 and the scaling block 803 are subtracted in subtract block 805 and the output goes to an absolute value amplifier 806. The output of the absolute value amplifier 806 goes to a comparator 807 that compares the data with the reference threshold "ϵ".

In another embodiment of decision circuit 800, if the comparator 807 output is high the sample from S/H 702 in FIG. 15 is kept and in case it is low the sample from S/H 702 is discarded and replaced by data from the S/H 701.

Figure 17:
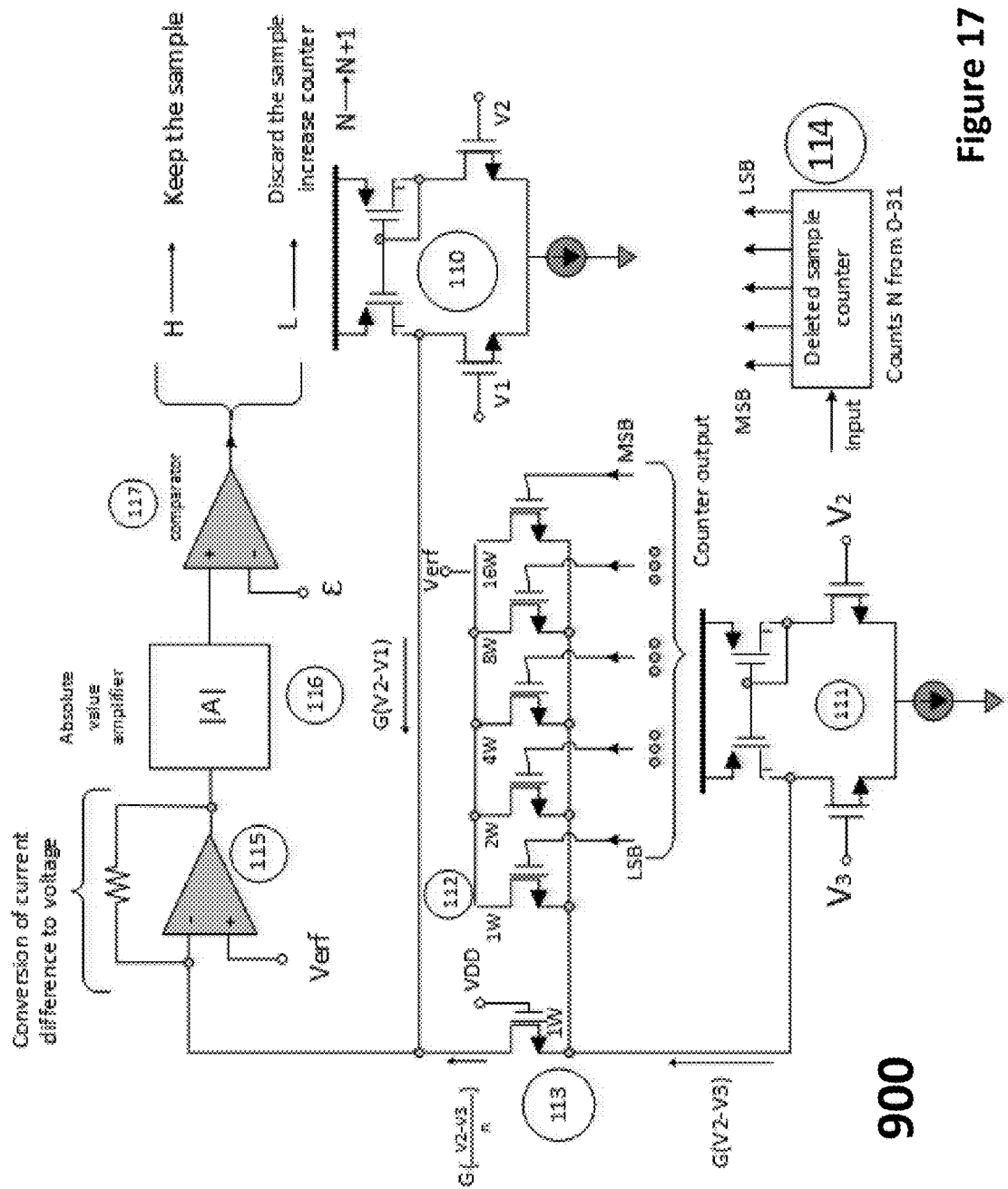
FIG. 17 depicts non-uniform sampling circuit diagram The drawings referred to in this description should be understood as not being drawn to scale except if specifically noted.

FIG. 17 depict implementation 900 as one possible implementation of decision circuit 800. The implementation 900 among others include subtract 110 and 111, counter 114, current splitter 112 and 113, current to voltage converter 115, absolute value amplifier 116 and comparator 117.

In one embodiment of implementation 900 the subtract 110 and 111 are voltage to current convertors and take V1, V2, and V2, V3 as their input and produce G(V2−V1) and G(V2−V3) at their outputs respectively.

In another embodiment of implementation 900 the counter 114 counts the number of deleted samples.

In one embodiment of implementation 900 the circuit 112 and 113 are current splitter which scales the output current of subtract 111 down proportional to the number of deleted samples and produce G(V2−V3)/n(number of discarded samples).

In one embodiment of implementation 900 the currents G(V2−V1) and G(V2−V3)/n add and produce G((V2−V3)/n+V2−V1).

In another embodiment of implementation 900 the resulting subtracted current G((V2−V3)/n+V2−V1) is converted back to voltage in the circuit 115.

In one embodiment of implementation 900 the output voltage of circuit 115 is applied to absolute amplifier 116 to produce the absolute of "AB" of FIG. 14.

In another embodiment of implementation 900 the amplified absolute value at the output of circuit 116 is compared with threshold "ϵ" in the comparator 117 and if the result is low the sample is discarded and the deleted sample counter is increased.

In one embodiment of implementation 900, the current splitter 112 and 113 is a new precise analog means to divide the incoming current by "n" which is the number of eliminated samples. In this example implementation, the drain of all the transistors are biased at Vref (a reference voltage) and their gates are connected to the delete sample counter 114 bits. The multiple transistors in 112 are binary scaled with the LSB of the counter coming to the gate of minimal sized transistor and the MSB goes to the gate of a device which is binary weighted in size.

In another embodiment of implementation 900, the voltage of the drain of scaling transistors 112 are all connected to Vref and the reference input of amplifier 115 is also connected to Vref. This forces the drain of transistor 113 to be also sitting at Vref. This design forces the current scaling to be quite perfect and not be affected by device nonlinearities.

Various embodiments are thus described. While particular embodiments have been described, it should be appreciated that the embodiments should not be construed as limited by such description, but rather construed according to the following claims.

The invention claimed is:

1. An analog circuit to perform a non-uniform sampling by eliminating a redundant sample comprising:
   a first sample and hold circuit that continuously takes a sample from an analog signal;
   a second sample and hold circuit that continuously takes said sample from said analog signal with a clock delay;
   a third sample and hold circuit that holds a sample that is not eliminated for further processing;
   a sample elimination circuit comprising:
   a first analog comparator to subtract a value of said sample from said first sample and hold circuit from a value of the sample from said second sample and hold circuit and produce a first output;
   a second analog comparator to subtract the value of said sample from said third sample and hold circuit from the value of the sample from the second sample and hold circuit and produce a second output;
   an eliminate sample counter that counts an eliminated sample and is incremented when one of said samples is eliminated;
   an analog scaling circuit to divide the second output of said second analog comparator by a number of said eliminated samples provided by said eliminate sample counter and produce a third output;
   a third analog comparator to subtract the first output from said third output to produce a fourth output;
   an absolute value amplifier to amplify the fourth output and produce a fifth output;
   a forth comparator to compare said fifth output with a reference threshold value to decide if the sample from said second sample and hold circuit can be eliminated or kept and sent to said third sample and hold circuit.

2. The analog circuit explained in claim 1, wherein said first analog comparator and the second analog comparator are voltage to current converters.

3. The analog circuit explained in claim 1, wherein said analog scaling circuit is a current splitter which scales down said second output proportional to the number of said eliminated samples and is represented by an array of transistors.

4. The analog circuit explained in claim 3, wherein said analog scaling circuit that divides said second output by the number of said eliminated samples uses said eliminate sample counter's bits at gates of said array of transistors and the drains of said array of transistors are biased at a reference voltage.

5. The analog circuit explained in claim 1, wherein said fourth comparator is a slope change detector circuit that uses said reference threshold value as a first input and the fifth output as a second input and indicates if the sample needs to be eliminated or kept and sent to said third sample and hold circuit.

* * * * *